United States Patent [19]
Krstenansky et al.

[11] Patent Number: 5,541,161
[45] Date of Patent: * Jul. 30, 1996

[54] STABILIZED SULFONATE, SULFATE, PHOSPHONATE AND PHOSPHATE DERIVATIVES OF HIRUDIN

[75] Inventors: John L. Krstenansky, Cincinnati; Simon J. T. Mao, Loveland, both of Ohio

[73] Assignee: Merrell Pharmaceuticals Inc., Cincinnati, Ohio

[*] Notice: The portion of the term of this patent subsequent to Mar. 9, 2010, has been disclaimed.

[21] Appl. No.: 123,576

[22] Filed: Sep. 17, 1993

Related U.S. Application Data

[63] Continuation of Ser. No. 963,243, Oct. 19, 1992, abandoned, which is a continuation of Ser. No. 859,234, Mar. 26, 1992, abandoned, which is a continuation of Ser. No. 769,567, Oct. 2, 1991, abandoned, which is a continuation of Ser. No. 479,317, Feb. 13, 1990, abandoned.

[51] Int. Cl.$^6$ .............................. A61K 38/00; C07K 7/06; C07K 7/08; C07K 7/10
[52] U.S. Cl. .............. 514/14; 530/324; 530/325; 530/327; 530/326; 514/15; 514/16
[58] Field of Search ............................ 514/15–16, 14, 514/12; 530/324, 328, 326

[56] References Cited

U.S. PATENT DOCUMENTS

| | | |
|---|---|---|
| 4,654,302 | 3/1987 | Fritz et al. |
| 4,668,662 | 5/1987 | Tripier ............................ 514/12 |
| 4,767,742 | 8/1988 | Dodt et al. ...................... 514/12 |
| 4,791,100 | 12/1988 | Kramer et al. .................. 514/12 |

FOREIGN PATENT DOCUMENTS

| | | |
|---|---|---|
| 0276014 | 7/1988 | European Pat. Off. |
| 0291981 | 11/1988 | European Pat. Off. |
| 0291982 | 11/1988 | European Pat. Off. |
| 0333356 | 9/1989 | European Pat. Off. |
| 0347376 | 12/1989 | European Pat. Off. |

OTHER PUBLICATIONS

Maraganore, et al, "Anticoagulant Activity of Synthetic Hirudin Peptides", *J. Biol. Chem.*, 264, 8692–8698, 1989.
Krstenansky, et al, C–Terminal Peptide alcohol, acid and amide analogs of desulfato hirudin 54–65 as antithrombin agents, Thrombosis Research, 54, 319–325, 1989.
Mao, et al, Interaction with thrombin: Indendification of a minimal binding domain of hirudin that inhibits clotting activity, Biochemistry, 27, 8170–8173, 1988.
Chemical Abstracts 52:21222 abstracting F. Markwardt, Z. Physiol. Chem. 306, 147–156 (1957).
Dodt, J., et al., FEBS Letters 165(2), 180–84 (1984).
Chang, J–y., et al., FEBS Letters 164(2), 307–313 (1983).
Derwent Abstract 86–162802/26, W. German Applic. No. 3445517, published Jun. 19, 1986, Gen–Bio Tec Ges Gen, assignee.
Dodt, J., et al., Biol. Chem. Hoppe–Seyler 366, 379–385 (1985).
Badgy, D., et al., Biol. Chem. Hoppe–Seyler 366, 379–385 (1985).
Pilat, M. J. P., et al., Fed. Proc. 45(6), 1494, 76th Annual Meeting, ASBC, Jun. 8–12 (1986).
Krstenansky, J. L., et al., FEBS Letters 211(1), 10–16 (1987).
Mao, S. J. T., et al., Anal. Biochem. 161, 514–518 (1987).
Cram, D. J., et al., Organic Chemistry, 2nd Edition, McGraw Hill, p. 609 (1964).
Owen, T. J., et al., J. Med. Chem., 31, 1009–1011 (1988).
Minar, E., et al., Klin Wochenschr Feb. 15;63(4):190–1 (1985) [abstract of].
Markwardt, F., et al., Thromb. Haemostasis, 52(2), 160–3 (1984) [abstract of].
Markwardt, F., et al., Thromb Haemost Jun. 28;47(3):226–9 (1982) [abstract of].
Markwardt, F., et al., Thromb Haemost Jun. 28;49(3):235–7 (1983) [abstract of].
Bajusz, S., et al., Proc. 18th European Peptide Symposium, 473–476 (1984).
Krstenansky et al., Biochim. Biophys. Acta 957, 53–59 (1988).
Sturzebecher, The Thrombin (R. Machovich, Ed.) vol. 1, 131–160, CRC Press, Boca Roton, FL (1984).
Hruby, V., Life Sciences 31, 189–199 (1982).

*Primary Examiner*—Christina Y. Chan
*Assistant Examiner*—S. G. Marshall
*Attorney, Agent, or Firm*—T. Helen Payne

[57] ABSTRACT

This invention relates to peptide derivatives which are useful anticoagulant agents.

28 Claims, No Drawings

STABILIZED SULFONATE, SULFATE, PHOSPHONATE AND PHOSPHATE DERIVATIVES OF HIRUDIN

CROSS-REFERENCE TO RELATED APPLICATION

This is a continuation of application Ser. No. 07/963,243, filed Oct. 19, 1992, now abandoned, which is a continuation of application Ser. No. 07/859,234, filed Mar. 26, 1992, now abandoned, which is a continuation of application Ser. No. 07/769,567, filed Oct. 2, 1991, now abandoned, which is a continuation of application Ser. No. 07/479,317, filed Feb. 13, 1990, now abandoned.

FIELD OF INVENTION

This invention relates to novel peptides which are useful anticoagulant agents.

BACKGROUND OF INVENTION

Anticoagulants are useful therapeutic agents in the pharmacological treatment of, for example, acute deep venous thrombosis, pulmonary embolism, acute arterial embolization of the extremities, myocardial infarction, and disseminated intravascular coagulation. Prophylactic administration of anticoagulants is believed to prevent a recurrence of embolism in patients with rheumatic or arteriosclerotic heart disease and to prevent certain thromboembolic complications of surgery. Administration of anticoagulants has also been indicated in the treatment of coronary artery and cerebrovascular disease. Arterial thrombosis, particularly in arteries supplying the heart muscle and brain, is a leading cause of death.

Hirudin is a 65 residue polypeptide isolated from the salivary glands of leeches. It is an anticoagulant agent, which is a thrombin specific inhibitor. Although quite potent, clinical use of hirudin isolated from leech extracts seems unlikely because of its limited quantity, expense and allergic reactions which commonly follow administration of any foreign protein of this size.

Applicant previously discovered a specific region of hirudin responsible for its anticoagulant activity. This region has been chemically synthesized and certain of its analogs appear to bind to the recognition site of thrombin but not the enzymatic cleavage site which is spatially separate. Binding of the synthetic peptides competitively prevents binding of the fibrinogen to the recognition site of thrombin, a prerequisite to fibrin production and clot formation. These previously reported peptides of the formula

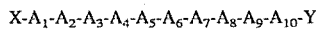

wherein
X is an amino terminal residue selected from hydrogen, one or two alkyl groups of from 1 to 6 carbon atoms, one or two acyl groups of from 2 to 10 carbon atoms, carbobenzyloxy or t-butyloxy carbonyl;
$A_1$ is a bond or is a peptide containing from 1 to 11 residues of any amino acid;
$A_2$ is Phe, SubPhe, β-(2- and 3-thienyl)alanine, β-( 2-and 3-furanyl)alanine, β-(2-, 3-, and 4-pyridyl)alanine, β-(benzothienyl-2- and 3-yl)alanine, β-(1- and 2-naphthyl)alanine, Tyr or Trp;
$A_3$ is Glu or Asp;
$A_4$ is any amino acid;
$A_5$ is Ile, Val, Leu, Nle, or Phe;
$A_6$ is Pro, Hyp, 3,4-dehydroPro, thiazolidine-4-carboxylate, Sar, NMePgl or D-Ala;
$A_7$ is any amino acid;
$A_8$ is any amino acid;
$A_9$ is a lipophilic amino acid selected from Tyr, Trp, Phe, Leu, Nle, Ile, Val, Cha and Pro or is a dipeptide containing at least one of these lipophilic amino acids;
$A_{10}$ is a bond or is a peptide fragment containing from one to five residues of any amino acid; and
Y is a carboxy terminal residue selected from OH, $C_1$-$C_6$ alkoxy, amino, mono- or di-($C_1$-$C_4$) alkyl substituted amino, or benzylamino;
possess significant anticoagulant activity. Applicant has now discovered a new class of modified peptides which retain the desirable therapeutic activity of the previously reported peptides but possess greater affinity for thrombin and/or greater stability to metabolic degradation.

SUMMARY OF THE INVENTION

A peptide derivative of formula 1

        1 wherein
X is an amino terminal residue selected from hydrogen, one or two alkyl groups of from 1 to 6 carbon atoms, one or two acyl groups of from 2 to 10 carbon atoms, carbobenzyloxy or t-butyloxy carbonyl;
$A_1$ is a bond, a peptide containing from 1 to 11 residues of any amino acid, or is $A_1'$;
$A_2$ is Phe, SubPhe, β-(2- and 3-thienyl)alanine, β-(2-and 3-furanyl)alanine, β-(2-, 3-, and 4-pyridyl)alanine, β-(benzothienyl-2- and 3-yl)alanine, β-(1- and 2-naphthyl)alanine, Tyr, Trp, or is $A_2'$;
$A_3$ is Glu, Asp, or $A_3'$;
$A_4$ is any amino acid or is $A_4'$;
$A_5$ is Ile, Val, Leu, Nle, or Phe;
$A_6$ is Pro, Hyp, 3,4-dehydroPro, thiazolidine-4-carboxylate, Sar, NMePgl or D-Ala;
$A_7$ is any amino acid or is $A_7'$;
$A_8$ is any amino acid or is $A_8'$;
$A_9$ is a lipophilic amino acid selected from Tyr, Trp, Phe, Leu, Nle, Ile, Val, Cha, Pro, or is a dipeptide containing at least one of these lipophilic amino acids, or is $A_9'$;
$A_{10}$ is a bond, a peptide fragment containing from one to five residues of any amino acid, or is $A_{10}'$ or a peptide fragment containing from one to five residues of any amino acid wherein one of the residues is $A_{10}'$; and
Y is a carboxy terminal residue selected from OH, $C_1$-$C_6$ alkoxy, amino, mono- or di-($C_1$-$C_4$) alkyl substituted amino, or benzylamino;
$A_1'$ is a group of the structure

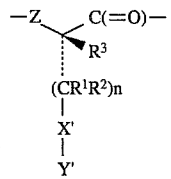

wherein n is an integer of from 1 to 2;
$R^1$, $R^2$, and $R^3$ are each independently selected from hydrogen and a methyl group;
X' is a —NH—, —O—, or —S— group, or a bond;

Y' is a —SO₃H or —PO₃H₂ group; and

Z is a bond or is a —NH—, —N(C₁-C₄alkyl)—, or a (C₁-C₄) alkyl group

A₂' is a group of the structure

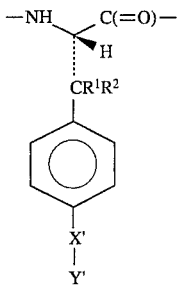

wherein R¹ and R² are each independently a hydrogen or methyl group;

X' is a —NH— or —O— group or a bond; and

Y' is a —SO₃H or —PO₃H₂ group;

A₃' and A₄' are each independently a group of the structure

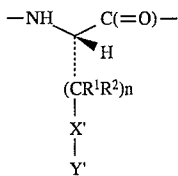

wherein n is an integer of from 1 to 3;

R¹ and R² are each independently a hydrogen or a methyl group;

X' is a —NH—, —O—, or —S— group or a bond; and

Y' is a —SO₃H or —PO₃H₂ group;

A₇' and A₈' are each independently a group of the structure

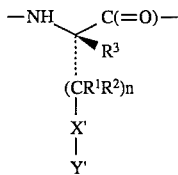

wherein n is an integer of from 1 to 3;

R¹, R², and R³ are each independently a hydrogen or a methyl group;

X' is a —NH—, —O—, or —S— group or a bond; and

Y' is a —SO₃H or —PO₃H₂ group;

A₉' is a group of the structure

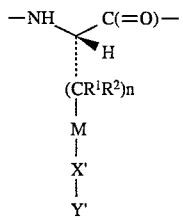

wherein R¹ and R² are each independently a hydrogen or methyl group;

M is a bond or a group of one of the formulae

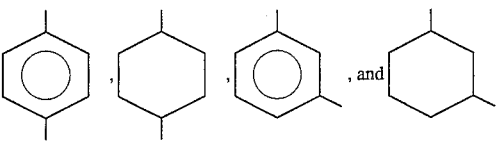

X' is a —NH— or —O— group or a bond; and

Y is a —SO₃H or —PO₃H₂ group;

A₁₀' can be selected from any of the members of A₁', A₂', A₃', A₄', A₇', A₈', and A₉' with the proviso that at least one of A₁, A₂, A₃, A₄, A₇, A₈, A₉, and A₁₀ must be selected from A₁', A₂', A₃', A₄', A₇', A₈', A₉', and A₁₀' respectively, and with the further proviso that when A₉' is Tyr (SO₃H) then at least one of A₁, A₂, A₃, A₄, A₇, A₈ and A₁₀ must be selected from A₁', A₂', A₃', A₄', A₇', A₈', and A₁₀', respectively, or a cationic salt or a pharmaceutically acceptable acid addition salt thereof are useful anticoagulant agents.

DETAILED DESCRIPTION OF THE INVENTION

The following common abbreviations of the amino acids are used throughout this specification:

Gly - glycine
Ala - alanine
Val - valine
Leu - leucine
Ile - isoleucine
Cha - cyclohexylalanine
Orn - ornithine
Pro - proline
Phe - phenylalanine
Trp - tryptophan
Met - methionine
Ser - serine
Thr - threonine
Cys - cysteine
Tyr - tyrosine
Asn - asparagine
Gln - glutamine
Asp - aspartic acid
Glu - glutaminc acid
Lys - lysine
Arg - arginine
His - histidine
Nle - norleucine
Hyp - hydroxyproline
Glt - glutaryl
Mal - maleyl
Npa-β-(2-naphthyl)alanine
3,4-dehydroPro - 3,4-dehydroproline
Tyr(SO₃H) - tyrosine sulfate
Pgl - phenylglycine
NMePgl - N-methyl-phenylglycine
Sat - sarcocine (N-methylglycine)
pSubPhe - para substituted phenylalanine
SubPhe - ortho, meta, or para, mono- or di- substituted phenylalanine DAla - D-alanine Ac - acetyl Suc - succinyl pClPhe - para-chloro-phenylalanine Pnh - p-aminophenylalanine Pno - para-nitro-phenylalanine.

An alkyl group and the alkyl portion of an alkoxy group is taken to include straight, branched, or cyclic alkyl groups, for example, methyl, ethyl, propyl, isopro- pyl, butyl, isobutyl, tert-butyl, pentyl, isopentyl, sec-pentyl, cyclopentyl, hexyl, isohexyl, cyclohexyl and cyclopentylmethyl. An acyl group of from 2 to 10 carbon atoms is taken to include straight, branched, cyclic, saturated and unsaturated acyl groups having 1 or 2 carbonyl moieties per group, for example, acetyl, benzoyl succinyl, maleyl, and glutaryl. A halogen group is a fluoro, chloro, bromo or iodo group.

The term "any amino acid" as used herein includes the naturally occurring amino acids as well as other "non-protein" α-amino acids commonly utilized by those in the peptide chemistry arts when preparing synthetic analogs of naturally occurring peptides. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, ornithine, and lysine. Examples of "non-protein" α-amino acids are norleucine, norvaline, alloisoleucine, homoarginine, thiaproline, dehydroproline, hydroxyproline (Hyp), homoserine, cyclohexylglycine (Chg), α-amino-n-butyric acid (Aba), cyclohexylalanine (Cha), aminophenylbutyric acid (Pba), phenylalanines substituted at the ortho, meta, or para positions of the phenyl moiety with one or two of the following, a ($C_1$-$C_4$) alkyl, ($C_1$-$C_4$) alkoxy, halogen, or nitro groups or substituted with a methylenedioxy group, β-2- and 3-thienylalanine, β-2- and 3-furanylalanine, β-2-, 3-, and 4-pyridylalanine, β-(benzothienyl-2- and 3-yl)alanine, β-(1-and 2-naphthyl)alanine, O-alkylated derivates of serine, threonine, or tyrosine, S-alkylated cysteine, the O-sulfate ester of tyrosine, 3,5-diiodotyrosine, and the D-isomers of the naturally occurring amino acids.

The term "lipophilic amino acid" includes Tyr, Phe, Leu, Nle, Ile, Val, His, and Pro.

The natural amino acids with the exception of glycine, contain a chiral carbon atom. Unless otherwise specifically indicated, the optically active amino acids, referred to herein, are of the L-configuration. For example, any of the amino acids of the $A_1$ or $A_{10}$ group can be of the D- or L-configuration. As is customary, the structure of peptides written out herein is such that the amino terminal end is on the left side of the chain and the carboxy terminal end is on the right side of the chain.

The peptide derivatives of this invention each contain a negatively charged group on one or two of the constituent amino acid side chains, that is, the side chains of $A_1'$ $A_2'$, $A_3'$, $A_4'$, $A_7'$ $A_8'$ $A_9'$ and $A_{10}'$. Of course, the compounds of this invention must be electrostatically neutral, and, thus, a positively charged counterion must be associated with each molecule of negatively charged peptide derivative so as to neutralize the charge of the peptide derivative. While any positively charged species can neutralize the negatively charged peptide derivative, applicant contemplates only the use of those cations which are pharmaceutically acceptable, that is, those cations that are not substantially toxic at the dosage administered to acheive the desired effect and do not independently possess significant pharmacological activity. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower)alkylpiperidine, and any other suitable amine. Sodium salts are preferred.

The polypeptides of formula 1 can also form pharmaceutically acid addition acceptable salts with any non-toxic, organic or inorganic acid. Illustrative inorganic acids which form suitable salts include hydrochloric, hydrobromic, sulphutic and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases.

As with any generic group of chemical compounds, certain groups are preferred. Applicants prefer those peptide derivatives of formula 1 wherein X is hydrogen, acetyl, or succinyl.

Also preferred are those formula 1 compounds wherein $A_1$ is a bond or is

Thr—Pro—Lys—Pro—Gln—Ser—His—Asn—Asp—Gly—Asp,
—Ser—Thr—Pro—Asn—Pro—Glu—Ser—His—Asn—Asn—Gly—Asp—,
—His—Asn—Asp—Gly—Asp—,
—Asn—Asp—Gly—Asp—,
—Asp—Gly—Asp—,
—Gly—Asp—, or
—Asp—;

$A_2$ is preferably Phe, β-2- or 3-thienylalanine, Tyr, Trp, Npa, pClPhe, or $A_2'$ wherein $A_2'$ is a Tyr($SO_3H$) or Phe(p$NH_2SO_3H$);

$A_3$, Glu or $A_3'$;

$A_4$, Glu, Asp, Pro, Ala or $A_4'$;

$A_5$, Ile, Leu;

$A_6$, Pro, Sar, D-Ala, Hyp or NMePgl;

$A_7$, Glu, Gln, Asp, Ala or $A_7'$;

$A_8$, Glu, Asp, Ala or $A_8'$;

$A_9$, Cha, Pro, Ala-Tyr, Ala-Cha, Tyr-Cha, Tyr-Leu, Ala-Phe, Tyr-Tyr or $A_9'$ wherein $A_9'$ is a Phe(pNH$SO_3H$);

$A_{10}$, Glu, Asn, Asp-Glu, Pro, Gln, Ala, a bond, D-Lys, Lys, D-Asp, Orn or $A_{10}'$; and Y, OH or $NH_2$.

More preferred are those peptide derivatives of formula 1 wherein

X is acetyl and $A_1$ is Gly-Asp or Asp, or

X is Suc and $A_1$ is a bond; and wherein $A_2$ is Tyr or $A_2'$ wherein $A_2'$ is Tyr(SO$_3$H) or Phe(pnHSO$_3$H);

$A_3$ is Glu;

$A_4$ is Glu or Pro;

$A_5$ is Ile;

$A_6$ is Pro;

$A_7$ is Glu;

$A_8$ is Glu or Ala;

$A_9$ is Ala, Cha, $A_9'$ or is Ala-$A_9'$, wherein $A_9'$ is Phe(pNHSO$_3$H);

$A_{10}$ is D-Glu; and

Y is OH or NH$_2$.

The proteins of this invention can be prepared by a variety of procedures readily known to those skilled in the art. Such procedures include the solid phase sequential and block synthesis, gene cloning and combinations of these techniques. The solid phase sequential procedure can be performed using established automated methods such as by use of an automated peptide sythesizer. In this procedure an α-amino protected amino acid is bound to a resin support. The resin support employed can be any suitable resin conventionally employed in the art for the solid phase preparation of polypeptides, preferably polystyrene which has been cross-linked with from 0.5 to about 3 percent divinyl benzene, which has been either chloromethylated or hydroxymethylated to provide sites for ester formation with the initially introduced α-amino protected amino acid.

An example of a hydroxymethyl resin is described by Bodanszky, et al., *Chem. Ind. (London)* 38, 1597–98 (1966). A chloromethylated resin is commercially available from Bio Rad Laboratories, Richmond, Calif., and the preparation of such a resin is described by Stewart et al., "Solid Phase Peptide Synthesis" (Freeman & Co., San Francisco 1969), Chapter 1, pp. 1–6. The protected amino acid can be bound to the resin by the procedure of Gisin, *Helv. Chem Acta*, 56, 1476 (1973). Many resin bound, protected amino acids are commercially available. As an example, to prepare a polypeptide of this invention wherein the carboxy terminal end is a Thr residue, a tert-butyloxycarbonyl (Boc) protected Thr bound to a benzylated, hydroxymethylated phenylacetamidomethyl (PAM) resin can be used and is commercially available.

Following the coupling of the a-amino protected amino acid to the resin support, the protecting group is removed using any suitable procedure such as by using trifluoroacetic acid in methylene chloride, trifluoroacetic acid alone, or HCl in dioxane. The deprotection is carried out at a temperature of between 0° C. and room temperature. Other standard cleaving reagents and conditions for removal of specific α-amino protecting groups may be used. After removal of the α-amino protecting group the other amino protected amino acids are coupled step-wise in the desired order. Alternatively, multiple amino acid groups may be coupled by the solution method prior to coupling with the resin supported amino acid sequence.

The α-amino protecting group employed with each amino acid introduced into the polypeptide sequence may be any such protecting group known to the art. Among the classes of α-amino protecting groups contemplated are (1) acyl type protecting groups such as: formyl, trifluoroacetyl, phthalyl, toluenesulfonyl (tosyl), benzenesulfonyl, nitro-phenylsulfenyl, tritylsulfenyl, o-nitrophenoxyacetyl and α-chlorobutyryl; (2) aromatic urethan type protecting groups such as benzyloxycarbonyl and substituted benzyloxycarbonyl, such as p-chlorobenzyloxycarbonyl, p-nitrobenzyl- carbonyl, p-bromobenzyloxycarbonyl, p-methoxybenzyloxycarbonyl, 1-(p-biphenylyl)-1-methylethoxycarbonyl, α, α-dimethyl-3,5-dimethoxybenzyloxycarbonyl and benzhydryloxycarbonyl; (3) aliphatic urethan protecting groups such as tert-butyloxycarbonyl (Boc), diisopropylmethoxycarbonyl, isopropyloxycarbonyl, ethoxycarbonyl and allyloxycarbonyl; (4) cycloalkyl urethan type protecting groups such as cyclopentyloxycarbonyl, adamantyloxycarbonyl and cyclohexyloxycarbonyl; (5) thio urethan type protecting groups such as phenylthiocarbonyl; (6) alkyl type protecting groups such as triphenylmethyl (trityl) and benzyl; and (7) trialkylsilane groups such as trimethylsilane. The preferred α-amino protecting group is tert-butyloxycarbonyl.

The selection of an appropriate coupling reagent is within the skill of the art. A particularly suitable coupling reagent where the amino acid to be added is Gln, Asn or Arg is N,N'-diisopropylcarbodiimide and 1-hydroxy-benzotriazole. The use of these reagents prevents nitrile and lactam formation. Other coupling agents are (1) carbodiimides (e.g., N,N'-dicyclohexylcarbodiimide and N-ethyl-N'-(γ-dimethylaminopropylcarbodiimide); (2) cyanamides (e.g., N,N-dibenzylcyanamide); (3) ketenimines; (4) isoxazolium salts (e.g., N-ethyl-5-phenyl-isoxazolium- 3'-sulfonate; (5) monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., Boc-Ala-O-Ala-Boc) and (8) nitrogen containing heterocyclic compounds having a hydroxy group on one ring nitrogen (e.g., N-hydroxyphthalimide, N-hydroxysuccinimide and 1-hydroxybenzotriazole). Other activating reagents and their use in peptide coupling are described by Kapoor, *J. Pharm. Sci.*, 59, pp. 1–27 (1970). Applicants prefer the use of the symmetrical anhydride as a coupling reagent for all amino acids except Arg, Asn and Gln.

Each protected amino acid or amino acid sequence is introduced into the solid phase reactor in about a four-fold excess and the coupling is carried out in a medium of dimethylformamide: methylene chloride (1:1) or in dimethylformamide alone or preferably methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser et al, *Analyt. Biochem.* 34, 595 (1970).

After the desired amino acid sequence has been obtained, the peptide is removed from the resin. This can be done by hydrolysis such as by treatment of the resin bound polypeptide with a solution of dimethyl sulfide, p-cresol and thiocresol in dilute aqueous hydrofluoric acid.

As is known in the art of solid phase peptide synthesis many of the amino acids bear functionalities requiring protection during the chain preparation. The use and selection of the appropriate protecting group is within the ability of those skilled in the art and will depend upon the amino acid to be protected and the presence of other protected amino acid residues on the peptide. The selection of such a side chain protecting group is critical in that it must be one which is not removed by cleavage during cleavage of the protecting group of the α-amino moiety. For example, suitable side chain protecting groups for lysine are benzyloxycarbonyl and substituted benzyloxycarbonyl, said substituent being selected from halo (e.g., chloro, bromo, fluoro) and nitro (e.g., 2-chlorobenzyloxycarbonyl, p-nitrobenzyloxy-carbonyl, 3,4-dichlorobenzyloxycarbonyl), tosyl, t-amyloxycarbonyl, t-butyloxycarbonyl and diisopropylmethoxycarbonyl. The alcoholic hydroxyl group of threonine and serine can be protected with an acetyl, benzoyl, tert-butyl, trityl, benzyl, 2,6-dichlorobenzyl or benzyloxycarbonyl group. The preferred protecting group is benzyl.

These groups can be removed by procedures well known in the art. Typically protecting group removal is done after the peptide chain synthesis is complete but the protecting groups can be removed at any other appropriate time.

Procedures for preparing the phosphylation are known from L. Otvas, Jr. et al., *Int. J. Pept. Protein Res.* 34:129–133 (1989); J. W. Perich et al., *Tet. Lett.* 27:1377–1380 (1986); *J. W. Perich et al. Tet. Lett.* 27:1373–1376 (1986). Procedures for preparing the sulfates are known from T. Nakahara, et al., *Anal. Bio. Chem.* 154:193–199 (1986) and J. Martinez, et al., *J. Med. Chem.* 25:589–593 (1982). Procedures for preparing the S-sulfates are known from R. D. Cole, *Met. Enzymol.* 11:206 (1967).

The anticoagulant dose of a peptide derivative of this invention is from 0.2 mg/kg to 250 mg/kg of patient body weight per day depending on the patient, the severity of the thrombotic condition to be treated and the peptide derivative selected. The suitable dose for a particular patient can be readily determined. Preferably from 1 to 4 daily doses would be administered typically with from 5 mg to 100 mg of active compound per dose.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats and mice.

Although some of the peptide derivatives may survive passage through the gut following oral administration, applicants prefer non-oral administration, for example, subcutaneous, intravenous, intramuscular or intraperitoneal; administration by depot injection; by implant preparation; or by application to the mucous membranes, such as, that of the nose, throat and bronchial tubes, for example, in an aerosol can containing a peptide derivative of this invention in a spray or dry powder form.

For parentral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

EXAMPLES

This invention is illustrated by the following, nonlimiting examples.

Example 1

Preparation of Suc-Tyr-Pro-Ile-Pro-Glu-Glu-Ala-Pnh($SO_3$)-D-Glu-OH

The peptide Suc-Tyr-Pro-Ile-Pro-Glu-Glu-Ala-Pno-D-Glu-OH was synthesized by solid-phase methods using 0.5 mmol of a 0.56 mmol/g Boc-D-Glu(Bzl) Merrifield resin. Double symmetrical anhydride couplings were performed with 2.0 mmol N-α-Boc-amino acid (Peptides International) except in the case of N-α-Boc-p-Nitrophenylalanine, which is coupled by the DCC/HOBT method. The side chain protection utilized was: Glu(Bzl), Tyr(2-BrZ). Upon completion of the synthesis of the N-α-Boc protection was removed with 50% trifluoroacetic acid in methylene chloride. The peptide was N-terminal capped with succinic anhydride in dimethyl formamide, washed four times with dimethyl formamide, washed four times with methylene chloride and dried in vacuo. The peptide was deprotected and cleaved from the resin with anhydrous HF containing 5% anisole at −5° C., for 45 minutes. The HF was removed in vacuo at −5° C., the peptide extracted from the resin with 50% aqueous acetonitrile and 30% aqueous acetic acid and lyophilized.

The peptide was purified by reverse phase HPLC on a Rainin Dynamax 21.4×250 mm C18 column with a 20 to 23% acetonitrile linear gradient over 15 minutes in 0.1% aqueous trifluoroacetic acid buffer. Purity was checked by analytic HPLC on a Vydac 218TP54 column (4.6×250 mm C18) with a 15 to 40% acetonitrile linear gradient, 1% per minute in 0.1% aqueous trifluoroacetic acid buffer; identity was confirmed by FAB mass spectroscopy and amino acid analysis.

The p-nitrophenyalanine of the purified peptide was reduced to p-aminophenylalanine with 10% Pd/C and dry ammonium formate in anhydrous methanol at room temperature under argon for 1 hour. The catalyst was filtered off, the solvent removed on a rotary evaporator at room temperature and the peptide dissolved in 50% acetonitrile then lyophilized. The peptide was purified as above using a 15–19% acetonitrile linear gradient; purity and identity were confirmed as above.

The dried p-aminophenyl peptide was converted to the p-sulfonylaminophenyl with sulfur trioxide pyridine complex in anhydrous puridine and dimethylformamide at room temperature under argon for 1 hour. The reaction was quenched with water, adjusted to pH 7 with saturated sodium carbonate solution and lyophilized. The peptide was purified by reverse phase HPLC on a Rainin Dynamax 21.4×250 mm C18 column with a 0 to 10% acetonitrile gradient over 15 minutes in 10 mM ammonium acetate buffer at pH 6.0. The pure fractions were combined and lyophilized then twice redissolved in deionized water and lyophilized. Identity was confirmed by analytic HPLC, positve and negative ion FAB-MS, and amino acid analysis; however, fragmentation could only be seen with positive ion FAB-MS where the sulfate amide was the first bond to break. Proton NMR and UV spectroscopy confirmed that the p-aminophenylalanine was sulfated and that the tyrosine residue remained unchanged.

The compounds of Examples 2–4 are prepared similarly.

Example 2

Suc-TVr(SO$_3$H)-Glu-Pro-Ile-Pro-Glu-Glu-Ala-Phe(pNHSO$_3$H)-D-Glu-OH

Example 3

Suc-Tyr-Glu-Pro-Ile-Pro-Glu-Glu-Phe(pNHSO$_3$H)-D-Glu-OH

Example 4

Suc-Phe(pNHSO$_3$H)-Glu-Pro-Ile-Pro-Glu-Glu-Ala-Cha-D-Glu-OH

Example 5

Suc-Tyr(SO$_3$H)-Glu-Pro-Ile-Pro-Glu-Glu-Ala-Cha-D-Glu-OH

Example 6

Suc-Phe-Glu-Pro-Ile-Pro-Glu-Glu-Ala-Tyr(SO$_3$H)-D-Glu-OH

Example 7

Suc-Phe-Glu-Pro-Ile-Pro-Glu-Glu-Tyr(SO$_3$H)-Leu-D-Glu-OH

Example 8

Suc-Tyr-Ser(SO$_3$H)-Pro-Ile-Pro-Ser(SO$_3$H)-Ser(SO$_3$H)-Ala-Cha-Ser(SO$_3$H)-OH

The properties for the peptides of Examples 1–8 are as follows.

$A_2$ is Phe, SubPhe, β-(2- and 3-thienyl)alanine, β-(2- and 3-furanyl)alanine, β-(2-, 3-, and 4-pyridyl)alanine, β-(benzothienyl-2- and 3-yl)alanine, β-(1- and 2-naphthyl)alanine, Tyr, Trp, or is $A_2'$;

$A_3$ is Glu, Asp, Pro, or $A_3'$;

$A_4$ is any amino acid or is $A_4'$;

$A_5$ is Ile, Val, Leu, Nle, Pro, or Phe;

$A_6$ is Pro, Glu, Hyp, 3,4-dehydroPro, thiazolidine-4-carboxylate, Sar, NMePgl or D-Ala;

$A_7$ is any amino acid or is $A_7'$;

$A_8$ is any amino acid or is $A_8'$;

$A_9$ is a lipophilic amino acid selected from Tyr, Trp, Phe, Leu, Nle, Ile, Val, Cha, Pro, Ala, Ala-Tyr(SO$_3$H), Tyr(SO$_3$H)-Leu, or is a dipeptide containing at least one of these lipophilic amino acids, or is $A_9'$;

$A_{10}$ is a bond, a peptide fragment containing from one to five residues of any amino acid, or is $A_{10}'$ or a peptide fragment containing from one to five residues of any amino acid wherein one of the residues is $A_{10}'$; and Y is a carboxy terminal residue selected from OH, $C_1$-$C_6$ alkoxy, amino, mono- or di-($C_1$-$C_4$) alkyl substituted amino, or benzylamino;

$A_1'$ is a group of the structure

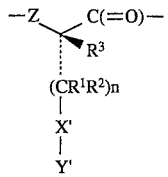

wherein n is an integer of from 1 to 2;

$R^1$, $R^2$, and $R^3$ are each independently selected from hydrogen and a methyl group;

X' is a —NH—, —O—, or —S— group or a bond;

| | AAA | | | | | | | Negative Ion FABMS | IC$_{50}$ Fibrin-Clot |
|---|---|---|---|---|---|---|---|---|---|
| Ser | Glu | Pro | Ala | Ile | Leu | Tyr | Phe | (M-H)$^-$ | Assay |
| 1 | — | 4.06 | 1.97 | 1.01 | 0.96 | — | 1.00 | — | 1416.2 | ++2.5 μM |
| 2 | — | 4.04 | 1.91 | 1.02 | 0.84 | — | 1.03 | — | 1496.7 | +15.0 μM |
| 3 | — | 4.08 | 1.96 | — | 0.95 | 1.00 | 1.01 | — | 1458.0 | 0.12 μM |
| 4 | — | 4.08 | 1.98 | 1.00 | 0.94 | — | — | — | 1406.7 | +13.0 μM |
| 5 | — | 4.06 | 1.97 | 1.00 | 0.96 | — | 1.01 | — | 1406.8 | ++1.7 μM |
| 6 | — | 4.06 | 1.98 | 1.00 | 0.95 | — | 0.99 | 1.02 | 1401.0 | — |
| 7 | — | 4.06 | 2.00 | — | 0.95 | 1.01 | 0.98 | 1.01 | 1443.1 | — |
| 8 | 4.02 | — | 1.94 | 1.06 | 0.93 | — | 1.05 | — | 1478.8 | ++0.21 μM |

++ < 5 μM
+ < 25 μM

We claim:

1. A peptide derivative of the formula

X-$A_1$-$A_2$-$A_3$-$A_4$-$A_5$-$A_6$-$A_7$-$A_8$-$A_9$-$A_{10}$-Y wherein X is an amino terminal residue selected from hydrogen, one or two alkyl groups of from 1 to 6 carbon atoms, one or two acyl groups of from 2 to 10 carbon atoms, carbobenzyloxy or t-butyloxy carbonyl;

$A_1$ is a bond, a peptide containing from 1 to 11 residues of any amino acid, or is $A_1'$;

Y' is a —SO$_3$H or —PO$_3$H$_2$ group; and

Z is a bond or is a —NH—, —N($C_1$-$C_4$ alkyl)—, or a ($C_1$-$C_4$) alkyl group $A_2'$ is a group of the structure

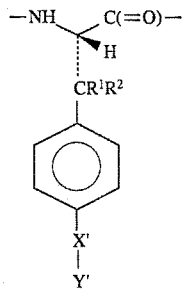

$R^1$ and $R^2$ are each independently a hydrogen or a methyl group;

X' is a —NH—, —O—, or —S— group or a bond; and

Y' is a —$SO_3H$ or —$PO_3H_2$ group;

$A_3'$ and $A_4'$ are each independently a group of the structure

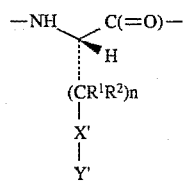

wherein n is an integer of from 1 to 3;

$R_1$ and $R_2$ are each independently hydrogen or a methyl group;

X' is a —NH—, —O—, or —S— group or a bond; or a bond

Y' is a —$SO_3H$ or —$PO_3H_2$ group;

$A_7'$ and $A_8'$ are each independently a group of the structure

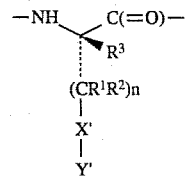

wherein n is an integer of from 1 to 3;

$R^1$, $R^2$, and $R^3$ are each independently a hydrogen or a methyl group;

X' is a —NH—, —O—, or —S— group or a bond; and

Y' is a —$SO_3H$ or —$PO_3H_2$ group;

$A_9'$ is a group of the structure

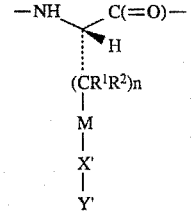

wherein $R^1$ and $R^2$ are each independently a hydrogen or methyl group;

M is a bond or a group of one of the formulae

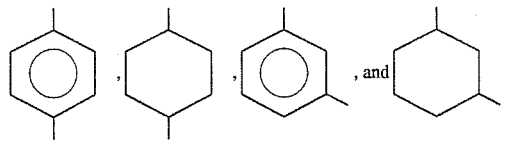

X' is a —NH— or —O— group or a bond; and

Y is a —$SO_3H$ or —$PO_3H_2$ group;

$A_{10}'$ can be selected from any of the members of $A_1'$, $A_2'$, $A_3'$, $A_4'$, $A_7'$, $A_8'$, and $A_9'$ with the proviso that at least one of $A_1$, $A_2$, $A_3$, $A_4$, $A_7$, $A_8$, $A_9$, and $A_{10}$ must be selected from $A_1'$, $A_2'$, $A_3'$, $A_4'$, $A_7'$, $A_8'$, $A_9'$, and $A_{10}'$, respectively, and with the further proviso that when $A_9'$ is Tyr($SO_3H$) then at least one of $A_1$, $A_2$, $A_3$, $A_4$, $A_7$, $A_8$ and $A_{10}$ must be selected from $A_1'$, $A_2'$, $A_3'$, $A_4'$, $A_7'$, $A_8'$, and $A_{10}'$, respectively, or a pharmaceutically acceptable acid addition salt thereof.

2. A peptide derivative of claim 1 wherein $A_2$ is Phe, β-(2- or 3-thienyl)alanine, Tyr, Trp, Npa, pClPhe, or $A_2'$ wherein $A_2'$ is a Tyr($SO_3H$) or Phe(p$NH_2SO_3H$).

3. A peptide derivative of claim 1 wherein $A_3$ is Glu or $A_3'$.

4. A peptide derivative of claim 1 wherein $A_4$ is Glu, Ala, Pro or $A_4'$.

5. A peptide derivative of claim 1 wherein $A_5$ is Ile or Leu.

6. A peptide derivative of claim 1 wherein $A_6$ is Pro, Ser, Ala, Hyp, or NMePgl.

7. A peptide derivative of claim 1 wherein $A_7$ is Glu, Gln, Asp, Ala, or $A_7'$.

8. A peptide derivative of claim 1 wherein $A_8$ is Glu, Asp, Ala, or $A_8'$.

9. A peptide derivative of claim 1 wherein $A_9$ is Cha, Pro, Tyr-Leu, Ala-Tyr, Ala-Cha, Tyr-Cha, Ala-Phe, Tyr-Tyr, or $A_9'$ wherein $A_9'$ is a Phe(p$NHSO_3H$).

10. A peptide derivative of claim 1 wherein $A_{10}$ is Gln, Asp, Pro, a bond, Asn, Asp-Glu, Glu, Ala, D-Lys, Lys, D-Asp, D-Glu, Orn, or $A_{10}'$.

11. A peptide derivative of claim 1 wherein X is H, acetyl, or succinyl.

12. A peptide derivative of claim 1 wherein Y is OH or $NH_2$.

13. A peptide derivative of claim 1 wherein $A_1$ is
—Gly—Asp,
—Asp, or
a bond.

14. A peptide derivative of claim 1 wherein $A_2$ is Tyr or $A_2'$ wherein $A_2'$ is Tyr($SO_3H$) or Phe(p$NH_2SO_3H$).

15. A peptide derivative of claim 1 wherein $A_3$ is Glu.

16. A peptide derivative of claim 1 wherein $A_4$ is Glu or Pro.

17. A peptide derivative of claim 1 wherein $A_5$ is Ile.

18. A peptide derivative of claim 1 wherein $A_6$ is Pro.

19. A peptide derivative of claim 1 wherein $A_7$ is Glu.

20. A peptide derivative of claim 1 wherein $A_8$ is Glu or Ala.

21. A peptide derivative of claim 1 wherein $A_9$ is Ala, Cha, A9', or Ala-Phe(p$NH_2SO_3H$).

22. A peptide derivative of claim 1 wherein $A_{10}$ is Glu.

23. A peptide derivative of claim 1 which is Suc-Tyr($SO_3H$)-Glu-Pro-Ile-Pro-Glu-Glu-Ala-Phe(p$NHSO_3H$)-Glu-OH.

24. A peptide derivative of claim 1 which is Suc-Tyr-Glu-Pro-Ile-Pro-Glu-Glu-Phe(p$NHSO_3H$)-Glu-OH.

25. A peptide derivative of claim 1 which is Suc-Phe(P$NHSO_3H$)-Glu-Pro-Ile-Pro-Glu-Glu-Ala-Cha-Glu-OH.

26. A peptide derivative of claim 1 which is Suc-Tyr(SO₃H)-Glu-Pro-Ile-Pro-Glu-Glu-Ala-Cha-D-Glu-OH.

27. A peptide derivative of claim 1 which is Suc-Tyr-Ser(SO₃H)-Pro-Ile-Pro-Ser(SO₃H)-Ser(SO₃H)-Ala-Cha-Ser(SO₃H)-OH.

28. A method of reducing blood coagulation in a patient in need thereof which comprises administering an anticoagulant effective amount of a peptide derivative of one of claims 1–22 or 23–26 and a pharmaceutically acceptable carrier.

* * * * *

UNITED STATES PATENT AND TRADEMARK OFFICE
CERTIFICATE OF CORRECTION

PATENT NO. : 5,541,161

DATED : July 30, 1996

INVENTOR(s) : John L. Krstenansky and Simon J.T. Mao

It is certified that error appears in the above-identified patent and that said Letters Patent is hereby corrected as shown below:

Column 4, Line 64 Patent reads "Sat" and should read -- Sar --.

Column 5, Line 10 Patent reads "isopro-pyl" and should read --isopropyl--.

Column 6, Line 6 Patent reads "acheive" and should read -- achieve --

Column 6, Line 22 Patent reads "sulphutic" and should read --sulphuric--.

Column 6, Line 54 Patent reads "($pNH_2SO_3H$)" and should read --($pNHSO_3H$)--.

Column 7, Line 3 Patent reads "($pnHSO_3H$) and should read -- ($pNHSO_3H$)--.

Column 7, Line 64 Patent reads "urethan" and should read --urethane--.

Column 8, Line 3 Patent reads "urethan" and should read --urethane--.

Column 8, Line 6 Patent reads "urethan" and should read --urethane--.

Column 8, Line 8 Patent reads "urethan" and should read --urethane--.

Column 8, Line 25 Patent reads "1,2,4-triazol" and should read --1,2,4-triazol- --.

Column 9, Line 19 Patent reads "*J.W. Perich*" and should read --J.W. Perich--.

Column 10, Line 22 Patent reads "which is" and should read --which was--.

Column 10, Line 55 Patent reads "puridine" and should read --pyridine--.

Column 11, Line 35 Patent reads "Ilc" and should read --Ile--.

Column 13, Line 59 Patent reads "($CR^1R^2$)n" and should read --$CR^1R^2$--.

Column 14, Line 21 Patent reads "Tyr, Trp, Npa, pClPhe, or $A_2^?$ " and should read --Tyr or $A_2'$ --.

Column 14, Line 22 Patent reads "($pNH_2SO_3H$)" and should read --($pNHSO_3H$)--.

UNITED STATES PATENT AND TRADEMARK OFFICE
CERTIFICATE OF CORRECTION

PATENT NO. : 5,541,161

DATED : July 30, 1996

INVENTOR(s) : John L. Krstenansky and Simon J.T. Mao

It is certified that error appears in the above-identified patent and that said Letters Patent is hereby corrected as shown below:

Column 14, Line 48 Patent reads "(pNH$_2$SO$_3$H)" and should read --(pNHSO$_3$H)--.

Column 14, Line 58 Patent reads "(pNH$_2$SO$_3$H)" and should read --(pNHSO$_3$H)--.

Column 16, Line 4 Patent reads "claims 1-22 or 23-26" and should read --claims 1-22, 24-27 or 30--.

Signed and Sealed this

Twenty-third Day of June, 1998

*Attest:*

BRUCE LEHMAN

*Attesting Officer*  *Commissioner of Patents and Trademarks*